(12) United States Patent
Kamimura et al.

(10) Patent No.: US 9,115,075 B2
(45) Date of Patent: Aug. 25, 2015

(54) METHOD FOR PRODUCING HYDROXYCARBOXYLIC ACID DERIVATIVE

(75) Inventors: Akio Kamimura, Yamaguchi (JP); Kouji Kaiso, Yamaguchi (JP); Tsunemi Sugimoto, Yamaguchi (JP)

(73) Assignees: YAMAGUCHI UNIVERSITY (JP); UBE INDUSTRIES, LTD (JP)

( * ) Notice: Subject to any disclaimer, the term of this patent is extended or adjusted under 35 U.S.C. 154(b) by 872 days.

(21) Appl. No.: 13/387,943

(22) PCT Filed: Jul. 12, 2010

(86) PCT No.: PCT/JP2010/061757
§ 371 (c)(1),
(2), (4) Date: Mar. 1, 2012

(87) PCT Pub. No.: WO2011/016313
PCT Pub. Date: Feb. 10, 2011

(65) Prior Publication Data
US 2012/0149937 A1    Jun. 14, 2012

(30) Foreign Application Priority Data
Aug. 5, 2009  (JP) ................. 2009-182530

(51) Int. Cl.
*C07C 67/31* (2006.01)
*C07C 51/06* (2006.01)
*C07C 67/20* (2006.01)

(52) U.S. Cl.
CPC ..................... *C07C 67/20* (2013.01)

(58) Field of Classification Search
None
See application file for complete search history.

(56) References Cited

FOREIGN PATENT DOCUMENTS

| | | |
|---|---|---|
| EP | 1 801 101 A1 | 6/2007 |
| EP | 1 980 551 A1 | 10/2008 |
| JP | 08-301843 | 11/1996 |
| JP | 2000-191638 | 7/2000 |
| JP | 2002-148253 | 5/2002 |
| JP | 2003-171356 | 6/2003 |
| JP | 2007-169256 | 7/2007 |
| WO | 2007/088756 A1 | 8/2007 |

OTHER PUBLICATIONS

Extended European Search Report which issued in connection with corresponding European Application No. 10806313.2 on Jun. 4, 2014.

*Primary Examiner* — Michael Barker
*Assistant Examiner* — Po-Chih Chen
(74) *Attorney, Agent, or Firm* — Clark Hill PLC

(57) ABSTRACT

To provide a method for the production of a hydroxycarboxylic acid derivative, by which a hydroxycarboxylic acid derivative, which can be reused in various applications, can be obtained from a polyamide at a high yield without consuming a large amount of energy. A method for the production of a hydroxycarboxylic acid derivative, which is characterized by including allowing an alcohol in a supercritical state to act on a polyamide in the presence of a carboxylic acid derivative to depolymerize the polyamide to obtain the hydroxycarboxylic acid derivative.

1 Claim, No Drawings

METHOD FOR PRODUCING HYDROXYCARBOXYLIC ACID DERIVATIVE

TECHNICAL FIELD

The present invention relates to a method for the production of a hydroxycarboxylic acid derivative that is useful as an intermediate material for organic synthesis, from a polyamide.

BACKGROUND ART

Polyamide products such as nylon 6 and nylon 12 are utilized in a large amount as nylon fibers, films and engineering plastics in various fields. Used polyamide products are treated in landfills or incineration as waste materials. However, various methods for recycling polyamide products have been considered in recent years from the viewpoints of environmental conservation and effective utilization of resources. For example, Patent Literature 1 describes a method including depolymerizing a polyamide in water in the presence of a nitrogen-containing compound. Furthermore, Patent Literature 2 describes a method for depolymerizing an ε-caprolactam oligomer to ε-caprolactam, which includes contacting the ε-caprolactam oligomer with water at a high temperature and a high pressure at a reaction temperature of from 280 to 450° C. and a pressure of from 100 to 500 kg/cm$^2$.

However, ε-caprolactam that is obtained by, for example, depolymerization of nylon 6, has little use other than utilization as a monomer for nylon 6. In view of chemical recycle, there is a problem that, when waste materials from nylon 6 are reused in various applications, the waste materials need to be decomposed into hydrogen, carbon monoxide, methane and the like, and a large amount of energy is consumed therefor.

On the other hand, hydroxycarboxylic acid derivatives such as 6-hydroxycaproic acid esters are useful as intermediate materials for general organic synthesis, and are specifically utilized in various applications such as cationic coagulants, intermediates for medicaments and agrochemicals, softening agents for synthetic fibers, anticorrosives and dispersing agents.

Therefore, the inventors have found a method for obtaining a 6-hydroxycaproic acid ester by acting an alcohol in a supercritical state on nylon 6 or the like, aiming at obtaining a hydroxycarboxylic acid derivative that can be reused in various applications from a polyamide without consuming a large amount of energy (Patent Literature 3).

CITATION LIST

Patent Literature

Patent Literature 1: Japanese Patent Application Laid-Open (JP-A) No. 8-301843
Patent Literature 2: JP-A No. 2000-191638
Patent Literature 3: International Publication No. 07/088756

DISCLOSURE OF INVENTION

Problem to be Solved by the Invention

However, the method described in Patent Literature 3 has a problem that the yield of the obtained 6-hydroxycaproic acid ester is not necessarily sufficient. Therefore, the present invention aims at providing a method for the production of a hydroxycarboxylic acid derivative, by which a hydroxycarboxylic acid derivative, which can be reused in various applications, can be obtained at a high yield from a polyamide without consuming a large amount of energy.

Means for Solving Problem

The present inventors have done intensive studies in order to achieve the above-mentioned object, and consequently found that a hydroxycarboxylic acid derivative, which can be reused in various applications, can be obtained at a high yield without consuming a large amount of energy, by acting an alcohol in a supercritical state on a polyamide in the presence of a carboxylic acid derivative to depolymerize the polyamide. Therefore, the present invention is a method for the production of a hydroxycarboxylic acid derivative, which is characterized by including allowing an alcohol in a supercritical state to act on a polyamide in the presence of a carboxylic acid derivative to depolymerize the polyamide to obtain the hydroxycarboxylic acid derivative.

Effect of the Invention

According to the method for the production of a hydroxycarboxylic acid derivative of the present invention, a hydroxycarboxylic acid derivative can be obtained at a fine yield from a polyamide. In conventional chemical recycle, waste materials from a polyamide such as nylon 6 are decomposed into hydrogen, carbon monoxide, methane and the like by consuming a large amount of energy, whereas according to the method for the production of a hydroxycarboxylic acid derivative of the present invention, a hydroxycarboxylic acid derivative that is a chemical raw material having a proceeded degree of processing and can be reused in various applications can be obtained from a waste material of a polyamide and the like at a high yield, and chemical recycle of a polyamide can be realized with lesser energy.

DESCRIPTION OF EMBODIMENTS

The polyamide used in the method for the production of a hydroxycarboxylic acid derivative of the present invention is a polymer that binds two or more amide (—C(=O)NH—) bonds. More specifically, it is a chain-like polymer form obtained by ring-opening polymerization of a monomer having a shape in which an amino group and a carboxyl group have been condensed by dehydration in one molecule to form a ring such as caprolactam. Furthermore, the polymerization degree of the polyamide is not specifically limited, and an oligomer having a low polymerization degree may also be used. Examples of the oligomer may include chain-like forms (from dimer to about heptamer of aminocaproic acid) and cyclic forms (from dimer to about nonamer). Furthermore, the polyamide may be one kind, or a mixture of two or more kinds. Examples may include nylon 6, nylon 11 and nylon 12 and the like, and nylon 6 is preferably used. Specific examples may include an irregular that is generated when the grade of a product is changed during the production of nylon 6 by continuously polymerizing a waste material from a nylon 6 fiber carpets or caprolactam; a residue including oligomers resulted from removal of water from washing water after hot-water washing of a polymerized product; a distillation residue that is generated during continuous distillation of caprolactam in the steps of the production of caprolactam as a monomer; and the like.

Examples of the alcohol used in the method for the production of a hydroxycarboxylic acid derivative of the present invention may include methanol, ethanol, 1-propanol(n-propanol), 2-propanol(isopropanol), allyl alcohol, 1-butanol(n-butanol), 2-butanol(sec-butanol), 2-methyl-1-propanol (isobutanol), 2-methyl-2-propanol(t-butanol), 3-buten-2-ol, crotyl alcohol, cyclopropanemethanol, 3-buten-1-ol, 2-methyl-2-propen-1-ol, 3-butyn-1-ol, 2-butyn-1-ol, 3-butyn-2-ol, 1-pentanol(n-pentanol), 2-pentanol(sec-amyl alcohol), 3-pentanol, 2-methyl-1-butanol, 2-methyl-2-butanol, 3-methyl-2-butanol, 3-methyl-1-butanol, 2,2-dimethyl-1-propanol(t-amyl alcohol), 1-cyclopropylethanol, 1-penten-3-ol, 4-penten-2-ol, 4-penten-1-ol, 3-penten-2-ol, 3-methyl-3-buten-1-ol, 2-methyl-3-buten-2-ol, 3-methyl-2-buten-1-ol, cyclobutanemethanol, 2-methylcyclopropanemethanol, 2-methyl-3-butene-1-ol, 2-methyl-3-butyn-2-ol, 2-pentyn-1-ol, 4-pentyn-2-ol, 4-pentyn-1-ol, 1,4-pentadien-3-ol, 2-pentyn-1-ol, 1-hexanol(n-hexanol), 2-hexanol, 3-hexanol, 3-methyl-3-pentanol, 4-methyl-1-pentanol, 4-methyl-2-pentanol, 3-methyl-1-pentanol, 2-methyl-2-pentanol, 3-methyl-2-pentanol, 2-methyl-3-pentanol, 2-methyl-1-pentanol, 2-ethyl-1-butanol, 2,3-dimethyl-2-butanol, 3,3-dimethyl-2-butanol, 3,3-dimethyl-1-butanol, cyclohexanol, 1-heptanol(n-heptanol), 2-heptanol, 3-heptanol, 2-methyl-3-hexanol, 2-methyl-2-hexanol, 5-methyl-1-hexanol, 5-methyl-1-hexanol, 2,2-dimethyl-3-pentanol, 3-ethyl-3-pentanol, 2,3-dimethyl-3-pentanol, 2,4-dimethyl-3-pentanol, 4,4-dimethyl-2-pentanol, 1-octanol(n-octanol), 2-octanol, 3-octanol, 6-methyl-2-heptanol, 4-methyl-3-heptanol, 2-ethyl-1-hexanol, 2,4,4-trimethyl-1-pentanol, 2-propyl-1-pentanol, 1-nonanol, 2-nonanol, 3-methyl-3-octanol, 2,6-dimethyl-4-heptanol, 3,5,5-trimethyl-1-hexanol, 3-ethyl-2,2-dimethyl-3-pentanol, 1-decanol(n-decanol), 2-decanol, 3,7-dimethyl-1-octanol, 3,7-dimethyl-3-octanol, 1-undecanol, 2-undecanol, 1-dodecanol(n-dodecanol), 2-dodecanol, 2-butyl-1-octanol, cyclododecanol, 1-tridecanol, 1-tetradecanol, 2-tetradecanol, 1-pentadecanol, 1-hexadecanol, 2-hexadecanol, 2-hexyl-1-decanol, 1-heptadecanol, 1-octadecanol and the like. Although the number of the carbon atoms in these alcohols is not specifically limited, primary alcohols are preferable, and examples may include chain-like aliphatic alcohols having 1 to 6 carbon atom(s) such as methanol, ethanol, n-propanol, n-butanol, n-pentanol and n-hexanol. Among these, primary alcohols such as methanol, ethanol, n-propanol, n-butanol, n-pentanol and n-hexanol are preferable, and methanol is specifically preferable.

These alcohols can be converted into a supercritical state by, for example, heating and pressurizing, or heating in a sealed state. In the method for the production of a hydroxycarboxylic acid derivative of the present invention, the alcohol may be converted into a supercritical state by heating or the like after simultaneously mixing the polyamide, alcohol and carboxylic acid, or the alcohol and carboxylic acid derivative may be mixed, converted into a supercritical state and added to the polyamide. The critical temperatures and critical pressures of major alcohols are as shown in Table 1.

TABLE 1

|  | Critical temperature (° C.) | Critical pressure (MPaG) |
|---|---|---|
| Methanol | 239 | 8.1 |
| Ethanol | 243 | 6.4 |
| n-Propanol | 264 | 5.2 |
| n-Butanol | 290 | 4.4 |

As the carboxylic acid derivative used for the method for the production of a hydroxycarboxylic acid derivative of the present invention, a carboxylic acid is preferable, and examples may include aliphatic carboxylic acids or aromatic carboxylic acids.

Examples of the aliphatic carboxylic acids may include aliphatic carboxylic acids having 1 to 12 carbon atom(s), preferably aliphatic carboxylic acids having 2 to 7 carbon atoms, and specific examples may include acetic acid, propionic acid, butyric acid, methoxyacetic acid, pentanoic acid, caproic acid, heptanoic acid, octanoic acid, lactic acid, glycolic acid and the like, preferably glycolic acid, lactic acid, acetic acid and methoxyacetic acid.

Examples of the aromatic carboxylic acid may include telephthalic acid, isophthalic acid, orthophthalic acid, trimellitic acid, benzoic acid, cresol acid, naphthoic acid, naphthalenedicarboxylic acid, and preferably benzoic acid.

The use amount of the carboxylic acid derivative is preferably from 1 to 1,000% by weight, more preferably from 10 to 500% by weight, with respect to the polyamide. When the use amount of the carboxylic acid derivative is small, the reaction velocity is decreased, and the yield of the hydroxycarboxylic acid derivative is decreased.

The reaction temperature is from 200 to 400° C., preferably 220° C. or more, and specifically preferably 250° C. or more. Furthermore, the reaction pressure is from 5 to 40 MPaG (wherein G represents a gauge pressure), preferably 8 MPaG or more. Furthermore, the reaction time is from 5 minutes to 48 hours, preferably from 0.5 hour to 24 hours.

The weight of the polyamide with respect to the total weight of the polyamide and alcohol is preferably more than 0 and 50% by weight or less, more preferably from 0.5 to 30% by weight, and specifically preferably from 1 to 25% by weight.

According to the method for the production of a hydroxycarboxylic acid derivative of the present invention, a hydroxycarboxylic acid derivative, in which, in the continuous units of the raw material polyamide having NH-sites and C(=O)-sites, the NH-sites have been converted to hydroxyl groups and the C(=O)-sites have been converted to the ester groups of the used alcohol, can be obtained. For example, when a reaction is conducted by acting methanol as an alcohol on nylon 6, methyl 6-hydroxycaproate can be obtained.

In a reaction liquid including a hydroxycarboxylic acid derivative obtained by the method for the production of a hydroxycarboxylic acid derivative of the present invention, an alcohol and a carboxylic acid ester (this represents a carboxylic acid ester generated by the reaction with the alcohol when a carboxylic acid is used as the carboxylic acid derivative) are removed by separation by flash distillation or the like. In the case when a hydroxycarboxylic acid derivative having a high purity is desired, it is purified by distilling under a reduced pressure the residue from which the alcohol and carboxylic acid ester have been removed by separation.

EXAMPLES

Next, the examples of the method for the production of a hydroxycarboxylic acid derivative of the present invention will be explained; however, the present invention is not limited to these Examples, and can be modified and carried out within the scope that does not depart from the gist of the present invention.

In the Examples, a reactor constituted by a stainless (SUS316) tube (outer diameter: ⅜ inches, inner diameter: 7.53 mm, length: 23 cm) and a two-end cap (SS-600-C, manufactured by Swagelok) and having a volume of 10 mL was prepared and used. In order to heat to a reaction temperature, an electric furnace (manufactured by ADVANTEC:

DRD360DA) was used. For gas chromatography measurements, GC-2014 manufactured by Shimadzu Corporation was used. The yield of each component in the reaction mixture was calculated based on [mol amount of each component]/[charged polyamide (g)/molecular weight of monomer]×100.

Example 1

Nylon 6 (0.1 g), glycolic acid as a carboxylic acid (0.380 g) and methanol (3.0 g) were added to a 10 mL volume reactor equipped with a tube (outer diameter: 3/8 inches, inner diameter: 7.53 mm, length: 23 cm), nitrogen substitution was conducted at room temperature, and the reactor was sealed. The reactor was put into an electric furnace heated to 300° C. (pressure: 16.1 MPa), and the change over time was measured. In the measurement, the obtained reaction mixture and 1-hexanol as an internal standard substance were weighed and used as analysis samples for a gas chromatography analysis. An integral value was calculated by a gas chromatography analysis, and a table of a standard curve was prepared and the yield of methyl 6-hydroxycaproate was obtained therefrom. The result is shown in Table 2.

TABLE 2

| Temperature (° C.) | Reaction time (min) | Yield (mol %) |
|---|---|---|
| 300 | 140 | 62 |
|  | 160 | 63 |
|  | 180 | 63 |

Example 2

Nylon 6 (0.1 g), methoxyacetic acid as a carboxylic acid (0.45 g) and methanol (3.0 g) were added to a 10 mL volume reactor equipped with a tube (outer diameter: 3/8 inches, inner diameter: 7.53 mm, length: 23 cm), nitrogen substitution was conducted at room temperature, and the reactor was sealed. The reactor was put into an electric furnace heated to 300° C. (pressure: 16.3 MPa), and the change over time was measured. In the measurement, the obtained reaction mixture and 1-hexanol as an internal standard substance were weighed and used as analysis samples for a gas chromatography analysis. An integral value was calculated by a gas chromatography analysis, and a table of a standard curve was prepared and the yield of methyl 6-hydroxycaproate was obtained therefrom. The result is shown in Table 3.

TABLE 3

| Temperature (° C.) | Reaction time (min) | Yield (mol %) |
|---|---|---|
| 300 | 240 | 55 |
|  | 300 | 55 |
|  | 360 | 61 |

Comparative Example 1

This was conducted in a similar manner to Example 1, except the change that the carboxylic acid was not added (pressure: 16.7 MPa). The result is shown in Table 4.

TABLE 4

| Temperature (° C.) | Reaction time (min) | Yield (mol %) |
|---|---|---|
| 300 | 140 | 2 |
|  | 160 | 4 |
|  | 180 | 4 |
|  | 240 | 8 |
|  | 300 | 12 |
|  | 360 | 16 |

Example 3

Nylon 6 (0.1 g), glycolic acid as a carboxylic acid (0.380 g) and methanol (3.0 g) were added to a 10 mL volume reactor equipped with a tube (outer diameter: 3/8 inches, inner diameter: 7.53 mm, length: 23 cm), nitrogen substitution was conducted at room temperature, and the reactor was sealed. The reactor was put into an electric furnace heated to 270° C. (pressure: 11.8 MPa), and the change over time was measured. In the measurement, the obtained reaction mixture and 1-hexanol as an internal standard substance were weighed and used as analysis samples for a gas chromatography analysis. An integral value was calculated by a gas chromatography analysis, and a table of a standard curve was prepared and the yield of methyl 6-hydroxycaproate was obtained therefrom. The result is shown in Table 5.

TABLE 5

| Temperature (° C.) | Reaction time (min) | Yield (mol %) |
|---|---|---|
| 270 | 240 | 65 |
|  | 360 | 63 |
|  | 420 | 66 |
|  | 480 | 67 |

Example 4

Nylon 6 (0.1 g), glycolic acid as a carboxylic acid (0.380 g) and methanol (3.0 g) were added to a 10 mL volume reactor equipped with a tube (outer diameter: 3/8 inches, inner diameter: 7.53 mm, length: 23 cm), nitrogen substitution was conducted at room temperature, and the reactor was sealed. The reactor was put into an electric furnace heated to 250° C. (pressure: 9.1 MPa), and the change over time was measured. In the measurement, the obtained reaction mixture and 1-hexanol as an internal standard substance were weighed and used as analysis samples for a gas chromatography analysis. An integral value was calculated by a gas chromatography analysis, and a table of a standard curve was prepared and the yield of methyl 6-hydroxycaproate was obtained therefrom. The result is shown in Table 6.

TABLE 6

| Temperature (° C.) | Reaction time (min) | Yield (mol %) |
|---|---|---|
| 250 | 540 | 69 |
|  | 720 | 65 |

Example 5

Nylon 6 (0.3 g), glycolic acid as a carboxylic acid (0.380 g) and methanol (3.0 g) were added to a 10 mL volume reactor equipped with a tube (outer diameter: ⅜ inches, inner diameter: 7.53 mm, length: 23 cm), nitrogen substitution was conducted at room temperature, and the reactor was sealed. The reactor was put into an electric furnace heated to 300° C., and a reaction was conducted for 3 hours (pressure: 17.0 MPa). Thereafter the reactor was taken out of the electric furnace and cooled rapidly in a cool water bath to stop the reaction. That the reactor had been cooled sufficiently was confirmed, and the reaction mixture was taken out by using methanol and collected. The obtained reaction mixture and 1-hexanol as an internal standard substance were weighed and used as analysis samples for a gas chromatography analysis. An integral value was calculated by a gas chromatography analysis, and a table of a standard curve was prepared and the yield was obtained therefrom. As a result, the yield of methyl 6-hydroxycaproate was 48%.

Example 6

Nylon 6 (0.5 g), glycolic acid as a carboxylic acid (0.380 g) and methanol (3.0 g) were added to a 10 mL volume reactor equipped with a tube (outer diameter: ⅜ inches, inner diameter: 7.53 mm, length: 23 cm), nitrogen substitution was conducted at room temperature, and the reactor was sealed. The reactor was put into an electric furnace heated to 300° C., and a reaction was conducted for 3 hours (pressure: 17.0 MPa). Thereafter the reactor was taken out of the electric furnace and cooled rapidly in a cool water bath to stop the reaction. That the reactor had been cooled sufficiently was confirmed, and the reaction mixture was taken out by using methanol and collected. The obtained reaction mixture and 1-hexanol as an internal standard substance were weighed and used as analysis samples for a gas chromatography analysis. An integral value was calculated by a gas chromatography analysis, and a table of a standard curve was prepared and the yield was obtained therefrom. As a result, the yield of methyl 6-hydroxycaproate was 46%.

Example 7

Nylon 6 (0.1 g), acetic acid as a carboxylic acid (0.300 g) and methanol (3.0 g) were added to a 10 mL volume reactor equipped with a tube (outer diameter: ⅜ inches, inner diameter: 7.53 mm, length: 23 cm), nitrogen substitution was conducted at room temperature, and the reactor was sealed. The reactor was put into an electric furnace heated to 330° C., and a reaction was conducted for 5 hours (pressure: 21.1 MPa). Thereafter the reactor was taken out of the electric furnace and cooled rapidly in a cool water bath to stop the reaction. That the reactor had been cooled sufficiently was confirmed, and the reaction mixture was taken out by using methanol and collected. The obtained reaction mixture and 1-hexanol as an internal standard substance were weighed and used as analysis samples for a gas chromatography analysis. An integral value was calculated by a gas chromatography analysis, and a table of a standard curve was prepared and the yield was obtained therefrom. As a result, the yield of methyl 6-hydroxycaproate was 50%.

Comparative Example 2

This was conducted in a similar manner to Example 7, except the change that the carboxylic acid was not added (pressure: 20.8 MPa). As a result, the yield of methyl 6-hydroxycaproate was 22%.

Example 8

Nylon 6 (0.1 g), lactic acid as a carboxylic acid (0.450 g) and methanol (3.0 g) were added to a 10 mL volume reactor equipped with a tube (outer diameter: ⅜ inches, inner diameter: 7.53 mm, length: 23 cm), nitrogen substitution was conducted at room temperature, and the reactor was sealed. The reactor was put into an electric furnace heated to 300° C. and a reaction was conducted for 3 hours (pressure: 16.1 MPa). Thereafter the reactor was taken out of the electric furnace and cooled rapidly in a cool water bath to stop the reaction. That the reactor had been cooled sufficiently was confirmed, and the reaction mixture was taken out by using methanol and collected. The obtained reaction mixture and 1-hexanol as an internal standard substance were weighed and used as analysis samples for a gas chromatography analysis. An integral value was calculated by a gas chromatography analysis, and a table of a standard curve was prepared and the yield was obtained therefrom. As a result, the yield of methyl 6-hydroxycaproate was 58%.

The invention claimed is:
1. A method for the production of an ester of hydroxycarboxylic acid, which is characterized by comprising allowing a primary alcohol in a supercritical state to react with a polyamide selected from the group consisting of nylon 6, nylon 11 and nylon 12 in the presence of a carboxylic acid to depolymerize the polyamide to obtain the ester of hydroxycarboxylic acid.

* * * * *